US012558548B2

(12) United States Patent
Zhang et al.

(10) Patent No.: US 12,558,548 B2
(45) Date of Patent: Feb. 24, 2026

(54) CLOSED LOOP STIMULATION ADJUSTMENTS BASED ON LOCAL AND SURROUND RECEPTIVE FIELD STIMULATION

(71) Applicant: Boston Scientific Neuromodulation Corporation, Valencia, CA (US)

(72) Inventors: Tianhe Zhang, Studio City, CA (US); Jianwen Gu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 390 days.

(21) Appl. No.: 17/929,564

(22) Filed: Sep. 2, 2022

(65) Prior Publication Data

US 2023/0072307 A1 Mar. 9, 2023

Related U.S. Application Data

(60) Provisional application No. 63/261,008, filed on Sep. 8, 2021.

(51) Int. Cl.
　　*A61N 1/36* (2006.01)
　　*A61N 1/05* (2006.01)
(52) U.S. Cl.
　　CPC ..... *A61N 1/36071* (2013.01); *A61N 1/36062* (2017.08); *A61N 1/0551* (2013.01)
(58) Field of Classification Search
　　CPC ............ A61N 1/36071; A61N 1/36062; A61N 1/0551; A61N 1/36139
　　See application file for complete search history.

(56) References Cited

U.S. PATENT DOCUMENTS 6,181,969 B1　1/2001　Gord
6,516,227 B1　2/2003　Meadows et al.
　　　　　　(Continued)

FOREIGN PATENT DOCUMENTS

WO　　2017/117421 A1　7/2017
WO　　2020/251899　　12/2020
　　　　　　(Continued)

OTHER PUBLICATIONS

Hillman, P., and P.D. Wall, "Inhibitory and Excitatory Factors Influencing the Receptive Fields of Lamina 5 Spinal Cord Cells," Experimental Brain Research, 9.4, 1969, pp. 284-306.
　　　　　　(Continued)

*Primary Examiner* — Benjamin J Klein
*Assistant Examiner* — Alisha J Sircar
(74) *Attorney, Agent, or Firm* — Lewis & Reese, PLLC

(57)　　　　　　ABSTRACT

Methods and systems for proving spinal cord stimulation (SCS) for treating pain in a patient are described. Embodiments of the described methods and systems can provide sub-perception SCS that has a fast wash-in time by using stimulation parameters that activate surround inhibition in the patient. Measuring retrograde potentials evoked by the stimulation can be performed to facilitate choosing the best stimulation parameters, in particular, the best stimulating electrode contact configurations for activating surround inhibition. For example, peripheral electrodes may be placed at the center of the patient's pain (within a local receptive field (LRF), with respect to the patient's pain center) and within an area surrounding the patient's pain center (within a surrounding receptive field (SRF), with respect to the patient's pain center). Retrograde evoked potentials measured and the SRF and/or the LRF can be used to guide the selection of the stimulation parameters.

18 Claims, 8 Drawing Sheets

(56)                    References Cited

U.S. PATENT DOCUMENTS

| | | | |
|---|---|---|---|
| 8,606,362 | B2 | 12/2013 | He et al. |
| 8,620,436 | B2 | 12/2013 | Parramon et al. |
| 9,259,574 | B2 | 2/2016 | Aghassian et al. |
| 9,302,112 | B2 | 4/2016 | Bornzin et al. |
| 9,314,202 | B2 | 4/2016 | Choi |
| 9,511,231 | B1 | 12/2016 | Kent et al. |
| 9,950,171 | B2 | 4/2018 | Johanek et al. |
| 10,406,368 | B2 | 9/2019 | Hershey et al. |
| 10,576,828 | B2 | 3/2020 | Thongam et al. |
| 10,894,158 | B2 | 1/2021 | Parker |
| 11,116,980 | B2 * | 9/2021 | Nelson ............... A61N 1/36071 |
| 12,138,457 | B2 * | 11/2024 | Wah ........................ A61B 5/388 |
| 2007/0213783 | A1 * | 9/2007 | Pless .................... A61N 5/0622 |
| | | | 607/42 |
| 2008/0154156 | A1 * | 6/2008 | Dellon ................. A61B 5/4041 |
| | | | 601/1 |
| 2012/0092031 | A1 | 4/2012 | Shi et al. |
| 2012/0095519 | A1 | 4/2012 | Parramon et al. |
| 2012/0095529 | A1 | 4/2012 | Parramon et al. |
| 2012/0278760 | A1 * | 11/2012 | Cerny .................. A61B 5/0031 |
| | | | 715/810 |
| 2013/0289665 | A1 | 10/2013 | Marnfeldt et al. |
| 2015/0080982 | A1 | 3/2015 | Funderburk |
| 2015/0157861 | A1 | 6/2015 | Aghassian |
| 2015/0231402 | A1 | 8/2015 | Aghassian |
| 2015/0360038 | A1 | 12/2015 | Zottola et al. |
| 2016/0022993 | A1 | 1/2016 | Grill et al. |
| 2016/0082261 | A1 * | 3/2016 | Moffitt ............... A61N 1/36132 |
| | | | 607/46 |
| 2018/0071520 | A1 | 3/2018 | Weerakoon et al. |
| 2018/0071527 | A1 | 3/2018 | Feldman et al. |
| 2018/0140831 | A1 | 5/2018 | Feldman et al. |
| 2019/0070418 | A1 | 3/2019 | Hincapie Ordonez et al. |
| 2019/0083796 | A1 | 3/2019 | Weerakoon et al. |
| 2019/0099601 | A1 * | 4/2019 | Torgerson ........... A61B 5/4848 |
| 2019/0099602 | A1 | 4/2019 | Esteller et al. |
| 2019/0134383 | A1 * | 5/2019 | Brill ........................ A61B 5/407 |
| 2019/0175915 | A1 | 6/2019 | Brill et al. |
| 2019/0175916 | A1 | 6/2019 | Grill et al. |
| 2019/0209844 | A1 * | 7/2019 | Esteller .............. A61N 1/36071 |
| 2019/0275331 | A1 | 9/2019 | Zhu |
| 2019/0290900 | A1 | 9/2019 | Esteller et al. |
| 2019/0299006 | A1 | 10/2019 | Marnfeldt |
| 2019/0336764 | A1 | 11/2019 | Simon et al. |
| 2019/0366094 | A1 | 12/2019 | Esteller et al. |
| 2019/0366104 | A1 | 12/2019 | Doan et al. |
| 2020/0147393 | A1 | 5/2020 | Zhang et al. |
| 2020/0155019 | A1 | 5/2020 | Esteller et al. |
| 2020/0305744 | A1 | 10/2020 | Weerakoon et al. |
| 2020/0305745 | A1 | 10/2020 | Wagenbach et al. |
| 2021/0387003 | A1 * | 12/2021 | Kelly ................. A61N 1/36139 |
| 2022/0062639 | A1 * | 3/2022 | Dinsmoor .......... A61N 1/36139 |
| 2022/0096840 | A1 * | 3/2022 | Li ........................ A61B 5/4836 |
| 2022/0266028 | A1 * | 8/2022 | Bink .................. A61N 1/36171 |
| 2023/0310867 | A1 * | 10/2023 | Single ............... A61N 1/36071 |
| | | | 607/62 |

FOREIGN PATENT DOCUMENTS

| | | |
|---|---|---|
| WO | 2021/026151 | 2/2021 |
| WO | 2021/080727 | 4/2021 |
| WO | 2021/178105 | 9/2021 |

OTHER PUBLICATIONS

Foreman, R.D. et al., "Effects of Dorsal Column Stimulation on Primate Spinothalamic Tract Neurons," Journal of Neurophysiology, 39.3, 1976, pp. 534-546.

Schoen, Nathan, et al., "The Use of Intraoperative Electromyogram During Spinal Cord Stimulator Placement Surgery: A Case Series," World Neurosurgery, 100, 2017, 74-84.

Zhang, Tianhe C., et al., "Modeling Effects of Spinal Cord Stimulation on Wide-Dynamic Range Dorsal Horn Neurons: Influence of Stimulation Frequency and GABAergic Inhibition," J. Neurophysiol. 115, pp. 552-567, 2014.

International Search Report and Written Opinion regarding corresponding PCT Application No. PCT/US2022/075927, mailed Nov. 25, 2022.

* cited by examiner

CLOSED LOOP STIMULATION ADJUSTMENTS BASED ON LOCAL AND SURROUND RECEPTIVE FIELD STIMULATION

CROSS REFERENCE TO RELATED APPLICATIONS

This application is a non-provisional of U.S. Provisional Patent Application Ser. No. 63/261,008, filed Sep. 8, 2021, which is incorporated herein by reference in its entirety, and to which priority is claimed.

FIELD OF THE INVENTION

This application relates to Implantable Medical Devices (IMDs), and more specifically sensing signals in an implantable stimulator device.

INTRODUCTION

Implantable neurostimulator devices are implantable medical devices (IMDs) that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application-specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as neuropathic pain. For example, SCS may be used to treat neuropathic pain in the patient's periphery, e.g., hands and/or feet.

IPG 10 can include an antenna 27a allowing it to communicate bi-directionally with a number of external devices used to program or monitor the IPG, such as a hand-held patient controller or a clinician's programmer, as described for example in U.S. Patent Application Publication 2019/0175915. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, MICS, and the like.

Stimulation in IPG 10 is typically provided by pulses each of which may include a number of phases such as 30a and 30b, as shown in the example of FIG. 2A. Stimulation parameters typically include amplitude (current I, although a voltage amplitude V can also be used); frequency (F); pulse width (PW) of the pulses or of its individual phases; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIGS. 2A and 2B, electrode E4 has been selected as an anode (during its first phase 30a), and thus provides pulses which source a positive current of amplitude +1 to the tissue. Electrode E5 has been selected as a cathode (again during first phase 30a), and thus provides pulses which sink a corresponding negative current of amplitude −I from the tissue. This is an example of bipolar stimulation, in which only two lead-based electrodes are used to provide stimulation to the tissue (one anode, one cathode). However, more than one electrode may be selected to act as an anode at a given time, and more than one electrode may be selected to act as a cathode at a given time. The case electrode Ec (12) can also be selected as an electrode, or current return, in what is known as monopolar situation.

IPG 10 as mentioned includes stimulation circuitry 28 to form prescribed stimulation at a patient's tissue. FIG. 3 shows an example of stimulation circuitry 28, which includes one or more current source circuits $40_i$ and one or more current sink circuits $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation. PDACs $40_i$ and NDACs $42_i$ can also comprise voltage sources.

Proper control of the PDACs $40_i$ and NDACs $42_i$ allows any of the electrodes 16 to act as anodes or cathodes to create a current through a patient's tissue, R, hopefully with good therapeutic effect. In the example shown (FIGS. 2A and 2B), and during the first phase 30a in which electrodes E4 and E5 are selected as an anode and cathode respectively, PDAC $40_4$ and NDAC $42_5$ are activated and digitally programmed to produce the desired current, I, with the correct timing (e.g., in accordance with the prescribed frequency F and pulse width PWa). During the second phase 30b (PWb), PDAC $40_5$ and NDAC $42_4$ would be activated to reverse the polarity of the current. More than one anode electrode and more than one cathode electrode may be selected at one time, and thus current can flow through the tissue R between two or more of the electrodes 16.

The stimulation circuitries described herein provide multiple independent current control (MICC) (or multiple independent voltage control) to guide the estimate of current fractionalization among multiple electrodes and estimate a total amplitude that provides a desired strength. In other words, the total anodic current can be split among two or more electrodes and/or the total cathodic current can be split among two or more electrodes, allowing the stimulation location and resulting field shapes to be adjusted. For example, a "virtual electrode" may be created at a position between two physical electrodes by fractionating current between the two electrodes. In other words, the virtual electrode is not co-located with any of the physical electrodes. Virtual electrodes may be created at positions between physical electrodes that are located on the same electrode lead or that are on different electrode leads.

Power for the stimulation circuitry 28 is provided by a compliance voltage VH. As described in further detail in U.S. Patent Application Publication 2013/0289665, the compliance voltage VH can be produced by a compliance voltage generator 29, which can comprise a circuit used to boost the battery 14's voltage (Vbat) to a voltage VH sufficient to drive the prescribed current I through the tissue R. The compliance voltage generator 29 may comprise an inductor-based boost converter as described in the '665 Publication, or can comprise a capacitor-based charge pump. Because the resistance of the tissue is variable, VH may also be variable, and can be as high as 18 Volts in one example.

Other stimulation circuitries 28 can also be used in the IPG 10. In an example not shown, a switching matrix can intervene between the one or more PDACs $40_i$ and the electrode nodes ei 39, and between the one or more NDACs $42_i$ and the electrode nodes. Switching matrices allow one or more of the PDACs or one or more of the NDACs to be connected to one or more anode or cathode electrode nodes at a given time. Various examples of stimulation circuitries can be found in U.S. Pat. Nos. 6,181,969, 8,606,362, 8,620,436, and U.S. Patent Application Publications 2018/0071520 and 2019/0083796. Much of the stimulation circuitry 28 of FIG. 3, including the PDACs $40_i$ and NDACs $42_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519, which are incorporated by reference. As explained in these references, ASIC(s) may also contain other circuitry useful in the IPG 10, such as telemetry circuitry (for interfacing off chip with telemetry antennas 27a and/or 27b), the compliance voltage generator 29, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Although not shown, circuitry in the IPG 10 including the stimulation circuitry 28 can also be included in an External Trial Stimulator (ETS) device which is used to mimic operation of the IPG during a trial period and prior to the IPG 10's implantation. An ETS device is typically used after the electrode array 17 has been implanted in the patient. The proximal ends of the leads in the electrode array 17 pass through an incision in the patient and are connected to the externally-worn ETS, thus allowing the ETS to provide stimulation to the patient during the trial period. Further details concerning an ETS device are described in U.S. Pat. No. 9,259,574 and U.S. Patent Application Publication 2019/0175915.

Referring again to FIG. 2A, the stimulation pulses as shown are biphasic, with each pulse at each electrode comprising a first phase 30a followed thereafter by a second phase 30b of opposite polarity. Biphasic pulses are useful to actively recover any charge that might be stored on capacitive elements in the electrode current paths, such as the DC-blocking capacitors 38, the electrode/tissue interface, or within the tissue itself. To recover all charge by the end of the second pulse phase 30b of each pulse (Vc4=Vc5=0V), the first and second phases 30a and 30b are preferably charged balanced at each electrode, with the phases comprising an equal amount of charge but of the opposite polarity. In the example shown, such charge balancing is achieved by using the same pulse width (PWa=PWb) and the same amplitude (|+I|=|−I|) for each of the pulse phases 30a and 30b. However, the pulse phases 30a and 30b may also be charged balance if the product of the amplitude and pulse widths of the two phases 30a and 30b are equal, as is known.

FIG. 3 shows that stimulation circuitry 28 can include passive recovery switches $41_i$, which are described further in U.S. Patent Application Publications 2018/0071527 and 2018/0140831. Passive recovery switches $41_i$ may be attached to each of the electrode nodes 39, and are used to passively recover any charge remaining on the DC-blocking capacitors Ci 38 after issuance of the second pulse phase 30b—i.e., to recover charge without actively driving a current using the DAC circuitry. Passive charge recovery can be prudent, because non-idealities in the stimulation circuitry 28 may lead to pulse phases 30a and 30b that are not perfectly charge balanced. Passive charge recovery typically occurs during at least a portion 30c (FIG. 2A) of the quiet periods between the pulses by closing passive recovery switches $41_i$. As shown in FIG. 3, the other end of the switches $41_i$ not coupled to the electrode nodes 39 are connected to a common reference voltage, which in this example comprises the voltage of the battery 14, Vbat, although another reference voltage could be used. As explained in the above-cited references, passive charge recovery tends to equilibrate the charge on the DC-blocking capacitors 38 and other capacitive elements by placing the capacitors in parallel between the reference voltage (Vbat) and the patient's tissue. Note that passive charge recovery is illustrated as small exponentially-decaying curves during 30c in FIG. 2A, which may be positive or negative depending on whether pulse phase 30a or 30b has a predominance of charge at a given electrode.

FIG. 4 shows various external devices that can wirelessly communicate data with the IPG 10 and/or the ETS 80, including a patient, hand-held external controller 45, and a clinician programmer 50. Both of devices 45 and 50 can be used to wirelessly send a stimulation program to the IPG 10 or ETS 80—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 80 is currently executing. Devices 45 and 50 may also receive information from the IPG 10 or ETS 80, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 80, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 80. For example, the external controller 45 can have a near-field magnetic-induction coil antenna 47a capable of wirelessly communicating with the coil antenna 27a or 42a in the IPG 10 or ETS 80. The external controller 45 can also have a far-field RF antenna 47b capable of wirelessly communicating with the RF antenna 27b or 42b in the IPG 10 or ETS 80.

The external controller 45 can also have control circuitry 48 such as a microprocessor, microcomputer, an FPGA, other digital logic structures, etc., which is capable of executing instructions in an electronic device. Control circuitry 48 can for example receive patient adjustments to stimulation parameters, and create a stimulation program to be wirelessly transmitted to the IPG 10 or ETS 80.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 80 can depend on the type of antennas included in those devices. If the patient's IPG 10 or ETS 80 includes a coil antenna 27a or 82a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 80. If the IPG 10 or ETS 80 includes an RF antenna 27b or 82b, the wand 54, the computing device 51, or both, can likewise include an RF antenna 56b to establish communication with the IPG 10 or ETS 80 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 80 (a process commonly referred to as "fitting" in the art), the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by controller circuitry 70 such as a microprocessor, microcomputer, an FPGA, other digital logic structures, etc., which is capable of executing programs in a computing device. In one example, controller circuitry 70 can include any of the i5 Core Processors, manufactured by Intel Corp. Such controller circuitry 70, in addition to executing the clinician programmer software 66 and rendering the GUI 64, can also enable communications via antennas 56a or 56b to communicate stimulation parameters chosen through the GUI 64 to the patient's IPG 10.

While GUI 64 is shown as operating in the clinician programmer 50, the user interface of the external controller 45 may provide similar functionality as the external controller 45 may have similar controller circuitry, software, etc.

SUMMARY

Disclosed herein is a method of providing sub-perception electrical stimulation to a patient's spinal cord to treat pain in the patient using one or more electrode leads implantable in the patient's spinal column, each electrode lead comprising a plurality of spinal electrode contacts, the method comprising: determining a first configuration of the spinal electrode contacts for providing sub-perception stimulation to the patient, wherein the first configuration is capable of providing stimulation that activates surround inhibition with respect to the pain, and using the first configuration of electrodes to provide stimulation to the patient, wherein the stimulation is below the patient's perception threshold, activates surround inhibition, and provides pain relief to the patient. According to some embodiments, the pain relief washes in in a period of one hour or less after beginning to provide the stimulation. According to some embodiments, the pain relief washes in in a period of ten minutes or less after beginning to provide the stimulation. According to some embodiments, determining the first configuration of the electrode contacts comprises: determining a locus of the pain, determining a surround receptive field (SRF) with respect to the locus, using a plurality of different trial configurations of the spinal electrode contacts to provide stimulation to the patient, for each trial configuration, recording neural responses evoked at the SRF for the stimulation using that trial configuration, and using the recorded SRF neural responses to determine the first configuration. According to some embodiments, determining the first configuration further comprises: determining a local receptive field (LRF) with respect to the locus, for each trial configuration, recording neural responses evoked at the LRF for the stimulation using that trial configuration, and using the recorded LRF neural responses and the recorded SRF neural responses to determine the first configuration. According to some embodiments, using the recorded LRF neural responses and the recorded SRF neural responses to determine the first configuration comprises using the recorded LRF neural responses and the recorded SRF neural responses to predict which of the trial configurations most strongly activates surround inhibition. According to some embodiments, using the recorded LRF neural responses and the recorded SRF neural responses to determine the first configuration comprises: determining a configuration that evokes the greatest SRF neural response and selecting that configuration as the first configuration. According to some embodiments, using the recorded LRF neural responses and the recorded SRF neural responses to determine the first configuration comprises: determining a configuration that evokes a ratio of SRF/LRF neural responses that exceeds a predetermined threshold value. According to some embodiments, using the recorded LRF neural responses and the recorded SRF neural responses to determine the first configuration comprises comparing one or more of the recorded LRF neural responses and the recorded SRF neural responses to a predetermined threshold. According to some embodiments, the method further comprises: for each trial configuration: using one or more of the spinal electrode contacts to record spinal neural responses evoked in the spinal cord by the stimulation that trial configuration, and saving a template comprising data indicative of the LRF neural response, the SRF neural response, and the spinal neural responses to stimulation at that trial configuration. According to some embodiments, the method further comprises: while providing sub-perception stimulation to the patient receiving an indication of a decline in efficacy of the stimulation, and using the template to adjust the stimulation. According to some embodiments, adjusting the stimulation comprises determining a second configuration of the spinal electrode contacts and using the second configuration to provide sub-perception stimulation to the patient. According to some embodiments, the method further comprises: using the first configuration to provide test stimulation the patient, and using one or more of the spinal electrode contacts to record spinal neural responses evoked in the spinal cord by the test stimulation. According to some embodiments, the method further comprises using the spinal neural responses in a closed-loop feedback control algorithm to adjust the sub-perception stimulation. According to some embodiments, adjusting the sub-perception stimulation comprises determining a second configuration of the spinal electrode contacts and using the second configuration to provide sub-perception stimulation to the patient.

Also disclosed herein is a system for providing sub-perception electrical stimulation to a patient's spinal cord to treat pain in the patient using one or more electrode leads implantable in the patient's spinal column, each electrode lead comprising a plurality of spinal electrode contacts, the system comprising: a neurostimulator that is connectable to the one or more electrode leads, and control circuitry configured to: determine a first configuration of the spinal electrode contacts for providing sub-perception stimulation to the patient, wherein the first configuration is capable of providing stimulation that activates surround inhibition with respect to the pain, and cause the neurostimulator to use the first configuration of electrodes to provide stimulation to the patient, wherein the stimulation is below the patient's perception threshold, activates surround inhibition, and provides pain relief to the patient. According to some embodiments, determining the first configuration of the electrode contacts comprises: determining a locus of the pain, determining a surround receptive field (SRF) with respect to the locus, using a plurality of different trial configurations of the spinal electrode contacts to provide stimulation to the patient, for each trial configuration, recording neural responses evoked at the SRF for the stimulation using that trial configuration, and using the recorded SRF neural responses to determine the first configuration. According to some embodiments, determining the first configuration further comprises: determining a local receptive field (LRF) with respect to the locus, for each trial configuration, recording neural responses evoked at the LRF for the stimulation using that trial configuration, and using the recorded LRF neural responses and the recorded SRF neural responses to determine the first configuration. According to some embodiments, using the recorded LRF neural responses and the recorded SRF neural responses to determine the first configuration comprises using the recorded LRF neural responses and the recorded SRF neural responses to predict which of the trial configurations most strongly activates surround inhibition. According to some embodiments, using the recorded LRF neural responses and the recorded SRF neural responses to determine the first configuration comprises: determining a configuration that evokes the greatest SRF neural response and selecting that configuration as the first configuration. According to some embodiments, using the recorded LRF neural responses and the recorded SRF neural responses to determine the first configuration comprises: determining a configuration that evokes a ratio of SRF/LRF neural responses that exceeds a predetermined threshold value. According to some embodiments, using the recorded LRF neural responses and the recorded SRF neural responses to determine the first configuration comprises comparing one or more of the recorded LRF neural responses and the recorded SRF neural responses to a predetermined threshold. According to some embodiments, the system is further configured to: for each trial configuration: use one or more of the spinal electrode contacts to record spinal neural responses evoked in the spinal cord by the stimulation that trial configuration, and save a template comprising data indicative of the LRF neural response, the SRF neural response, and the spinal neural responses to stimulation at that trial configuration. According to some embodiments, the system is further configured to: while providing sub-perception stimulation to the patient receive an indication of a decline in efficacy of the stimulation, and use the template to adjust the stimulation. According to some embodiments, adjusting the stimulation comprises determining a second configuration of the spinal electrode contacts and using the second configuration to provide sub-perception stimulation to the patient. According to some embodiments, the system is further configured to: use the first configuration to provide test stimulation the patient, and use one or more of the spinal electrode contacts to record spinal neural responses evoked in the spinal cord by the test stimulation. According to some embodiments, the system is further configured to use the spinal neural responses in a closed-loop feedback control algorithm to adjust the sub-perception stimulation. According to some embodiments, adjusting the sub-perception stimulation comprises determining a second configuration of the spinal electrode contacts and using the second configuration to provide sub-perception stimulation to the patient. According to some embodiments, the system is configured to record neural responses evoked at a surround receptive field (SRF), wherein the SRF is determined with respect to a locus of the pain and use the recorded SRF neural responses to determine the first configuration. According to some embodiments, the system is configured to record neural responses evoked at a local receptive field (LRF), wherein the LRF is determined with respect to a locus of the pain and u se the recorded LRF neural response and the recorded SRF neural responses to determine the first configuration.

Also disclosed herein is a method of providing electrical stimulation to a patient's spinal cord to treat peripheral pain in the patient using one or more electrode leads implantable in the patient's spinal column, each electrode lead comprising a plurality electrode contacts, the method comprising: determining a local receptive field (LRF) at the patient's periphery corresponding to a location of the patient's pain and a surrounding receptive field (SRF) at the patient's periphery corresponding to an area surrounding the location of the patient's pain, using a plurality of different configurations of the electrode contacts to provide stimulation to the patient's spinal cord, for each configuration, recording neural responses at the LRF and at the SRF, and using the neural responses at the LRF and at the SRF to determine an appropriate configuration of the electrode contacts to provide therapeutic stimulation to the patient.

Also disclosed herein is a system for providing sub-perception electrical stimulation to a patient's spinal cord to treat pain in the patient using one or more electrode leads implantable in the patient's spinal column, each electrode lead comprising a plurality of spinal electrode contacts, the system comprising: a neurostimulator that is connectable to the one or more electrode leads, and control circuitry configured to: determine a local receptive field (LRF) at the patient's periphery corresponding to a location of the patient's pain and a surrounding receptive field (SRF) at the patient's periphery corresponding to an area surrounding the location of the patient's pain, use a plurality of different configurations of the electrode contacts to provide stimulation to the patient's spinal cord, for each configuration, record neural responses at the LRF and at the SRF, and use the neural responses at the LRF and at the SRF to determine an appropriate configuration of the electrode contacts to provide therapeutic stimulation to the patient.

Also disclosed herein is a method of providing electrical stimulation to a patient's spinal cord to treat peripheral pain in the patient using one or more electrode leads implantable in the patient's spinal column, each electrode lead comprising a plurality electrode contacts, the method comprising: determining a local receptive field at the patient's periphery corresponding to a location of the patient's pain and a surrounding receptive field at the patient's periphery corresponding to an area surrounding the location of the patient's pain, using different configurations of the electrode contacts to provide stimulation to the patient's spinal cord, for each configuration, recording local neural responses at the local receptive field, surround neural responses at the surrounding receptive field, and spinal neural responses at one or more of the plurality of electrode contacts, correlating each of the local neural responses and the surround neural responses with the spinal neural responses, and using the correlations to program stimulation for the patient.

The invention may also reside in the form of a programed external device (via its control circuitry) for carrying out the above methods, a programmed IPG or ETS (via its control circuitry) for carrying out the above methods, a system including a programmed external device and IPG or ETS for carrying out the above methods, or as a computer readable media for carrying out the above methods stored in an external device or IPG or ETS.

DETAILED DESCRIPTION

Figure 5:
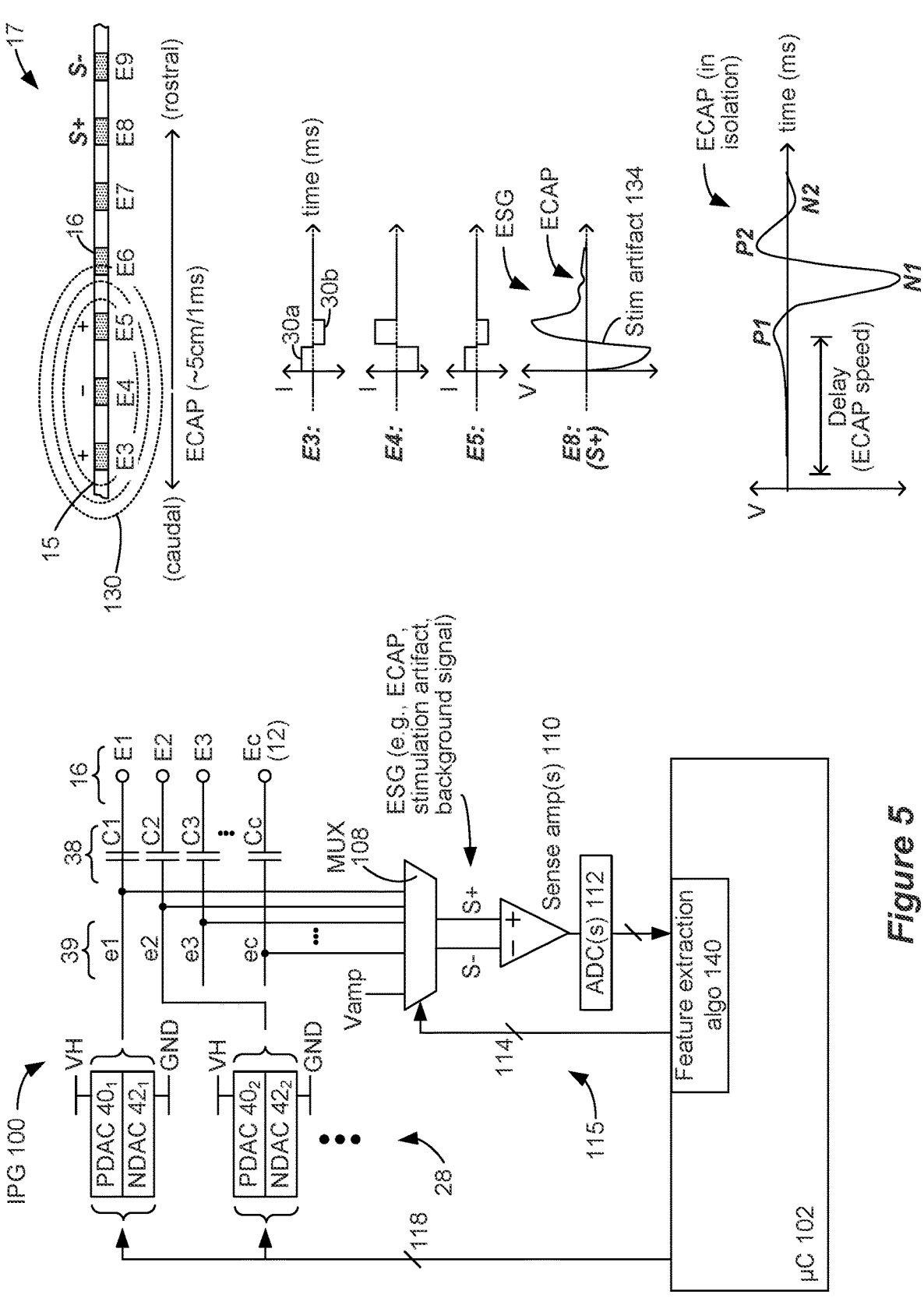
FIG. 5 shows an improved IPG having stimulation capability and the ability to sense an ElectroSpinoGram (ESG) signal which may include Evoked Compound Action Potentials (ECAPs) caused by the simulation.

An increasingly interesting development in pulse generator systems, and in Spinal Cord Stimulator (SCS) pulse generator systems specifically, is the addition of sensing capability to complement the stimulation that such systems provide. FIG. 5 shows an IPG 100 that includes stimulation and sensing functionality. An ETS as described earlier could also include stimulation and sensing capabilities, and the circuitry shown in FIG. 5.

For example, it can be beneficial to sense a neural response in neural tissue that has received stimulation from the IPG 100. One such neural response is an Evoked Compound Action Potential (ECAP). An ECAP comprises a cumulative response provided by neural fibers that are recruited by the stimulation, and essentially comprises the sum of the action potentials of recruited neural elements (ganglia or fibers) when they "fire." An ECAP is shown in isolation in FIG. 5, and comprises a number of peaks that are conventionally labeled with P for positive peaks and N for negative peaks, with P1 comprising a first positive peak, N1 a first negative peak, P2 a second positive peak, N2 a second negative peak, and so on. Note that not all ECAPs will have the exact shape and number of peaks as illustrated in FIG. 5, because an ECAP's shape is a function of the number and types of neural elements that are recruited and that are involved in its conduction. An ECAP is generally a small signal, and may have a peak-to-peak amplitude on the order of hundreds of microvolts or more.

FIG. 5 also shows an electrode array 17 comprising (in this example) a single percutaneous lead 15, and shows use of electrodes E3, E4 and E5 to produce pulses in a tripolar mode of stimulation, with (during the first phase 30a) E3 and E5 comprising anodes and E4 a cathode. Other electrode arrangements (e.g., bipoles, etc.) could be used as well. Such stimulation produces an electric field 130 in a volume of the patient's tissue centered around the selected electrodes. Some of the neural fibers within the electric field 130 will be recruited and fire, particularly those proximate to the cathodic electrode E4, forming ECAPs which can travel both rostrally toward the brain and caudally away from the brain. The ECAPs pass through the spinal cord by neural conduction with a speed which is dependent on the neural fibers involved in the conduction. In one example, the ECAP may move at a speed of about 5 cm/1 ms. U.S. Patent Application Publication 2020/0155019 describes a lead that can be useful in the detection of ECAPs.

ECAPs can be sensed at one or more sensing electrodes which can be selected from the electrodes 16 in the electrode array 17. Sensing preferably occurs differentially, with one electrode (e.g., S+, E8) used for sensing and another (e.g., S−, E9) used as a reference. This could also be flipped, with E8 providing the reference (S−) for sensing at electrode E9 (S+). Although not shown, the case electrode Ec (12) can also be used as a sensing reference electrode S−. Sensing reference S− could also comprise a fixed voltage provided by the IPG 100 (e.g., Vamp, discussed below), such as ground, in which case sensing would be said to be single-ended instead of differential.

The waveform appearing at sensing electrode E8 (S+) is shown in FIG. 5, which includes a stimulation artifact 134 as well as an ECAP. The stimulation artifact 134 comprises a voltage that is formed in the tissue as a result of the stimulation, i.e., as a result of the electric field 130 that the stimulation creates in the tissue. As described in U.S. Patent Application Publication 2019/0299006, the voltage in the tissue can vary between ground and the compliance voltage VH used to power the DACs, and so the stimulation artifact 134 can be on the order of Volts, and therefore significantly higher than the magnitude of stimulation-induced ECAPs. Generally speaking, the waveform sensed at the sensing electrode may be referred to as an ElectroSpinoGram (ESG) signal, which comprises the ECAP, the stimulation artifact 134, and other background signals that may be produced by neural tissue even absent stimulation. Realize that the ESG signal as shown at the sensing electrode S+ in FIG. 5 is idealized. The figures in International Patent Application Publication No. WO 2020/251899, show actual recorded ESG traces.

The magnitudes of the stimulation artifact 134 and the ECAP at the sensing electrodes S+ and S− are dependent on many factors, such as the strength of the stimulation, and the distance of sensing electrodes from the stimulation. ECAPs tend to decrease in magnitude at increasing stimulation-to-sensing distances because they disperse in the tissue. Stimulation artifacts 134 also decrease in magnitude at increasing stimulation-to-sensing distances because the electric field 130 is weaker at further distances. Note that the stimulation artifact 134 is also generally larger during the provision of the pulses, although it may still be present even after the pulse (i.e., the last phase 30b of the pulse) has ceased, due to the capacitive nature of the tissue or the capacitive nature of the driving circuitry (i.e., the DACs). As a result, the electric field 130 may not dissipate immediately upon cessation of the pulse.

It can be useful to sense in the IPG 100 features of either or both of the ECAPs or stimulation artifact 134 contained within the sensed ESG signal, because such features can be used to useful ends. For example, ECAP features can be used for feedback, such as closed-loop feedback, to adjust the stimulation the IPG 100 provides. See, e.g., U.S. Pat. No. 10,406,368; U.S. Patent Application Publications 2019/0099602, 2019/0209844, 2019/0070418, 2020/0147393; and International Patent Application Publication No. WO 2021/080727. ECAP assessment can also be used to infer the types of neural elements or fibers that are recruited, which can in turn be used to adjust the stimulation to selectively stimulate such elements. See, e.g., U.S. Patent Application Publication 2019/0275331. Assessments of ECAP features can also be used to determine cardiovascular effects, such as a patient's heart rate. See, e.g., U.S. Patent Application Publication 2019/0290900. To the extent one wishes to assess features of an ECAP that are obscured by a stimulation artifact, U.S. Patent Application Publication 2019/0366094 discloses techniques that can used to extract ECAP features from the ESG signal. As discussed in some of these references, detected ECAPs can also be dependent on a patient's posture or activity, and therefor assessment of ECAP features can be used to infer a patient's posture, which may then in turn be used to adjust the stimulation that the IPG 100 provides.

It can also be useful to detect features of stimulation artifacts 134 in their own right. For example, International Patent Application Publication WO 2020/251899 describes that features of stimulation artifacts can be useful to determining patient posture or activity, which again may then in turn be used to adjust the stimulation that the IPG 100 provides.

FIG. 5 shows further details of the circuitry in an IPG 100 that can provide stimulation and sensing an ElectroSpino-Gram (ESG) signal. The IPG 100 includes control circuitry 102, which may comprise a microcontroller, such as Part Number MSP430, manufactured by Texas Instruments, Inc., which is described in data sheets at www.ti.com, which are incorporated herein by reference. Other types of controller circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), such as those described and incorporated earlier.

Figures 1, 2A, 2B:
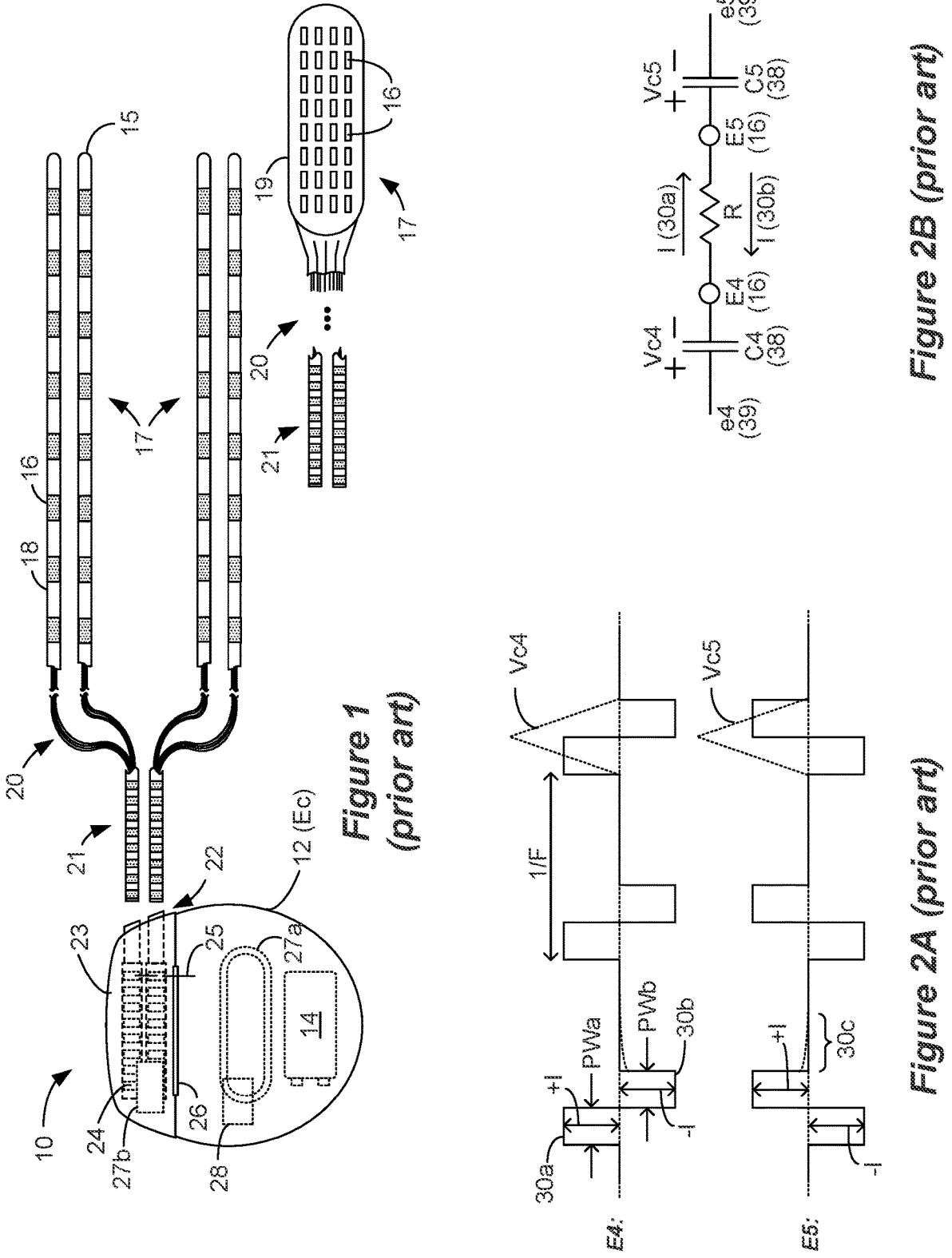
FIG. 1 shows an Implantable Pulse Generator (IPG), in accordance with the prior art.
FIGS. 2A and 2B show an example of stimulation pulses producible by the IPG, in accordance with the prior art.
Figure 3:
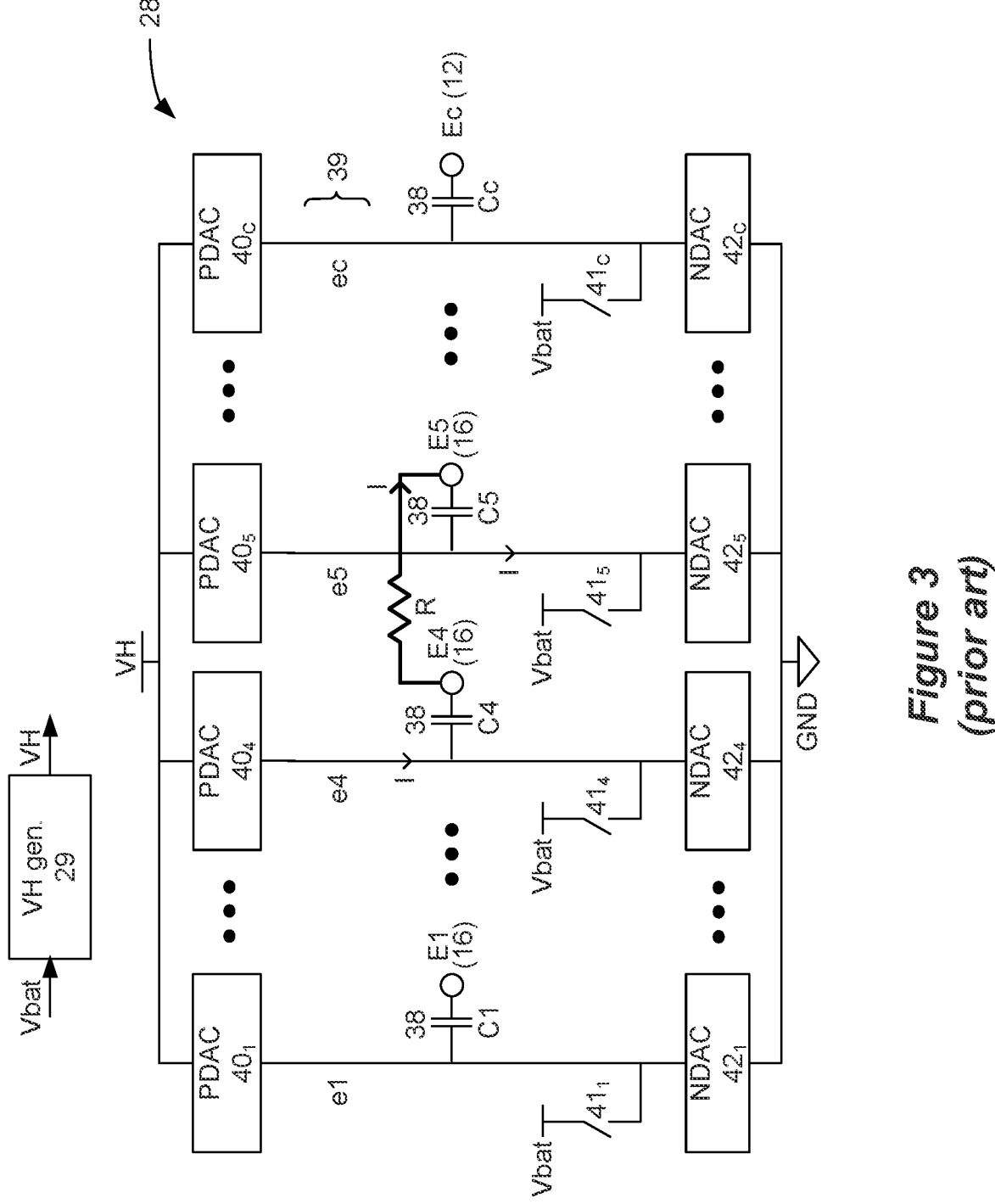
FIG. 3 shows stimulation circuitry useable in the IPG, in accordance with the prior art.
Figure 4:
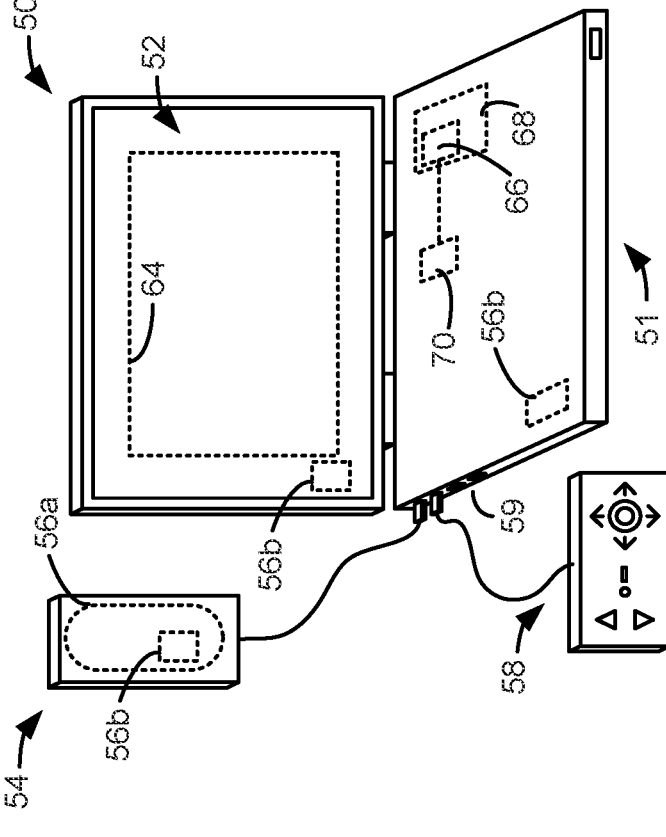
FIG. 4 shows external devices able to communicate with the IPG, in accordance with the prior art.
Figure 4:
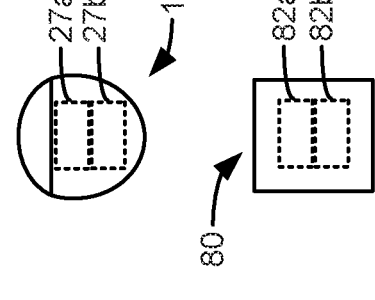
Figure 4:
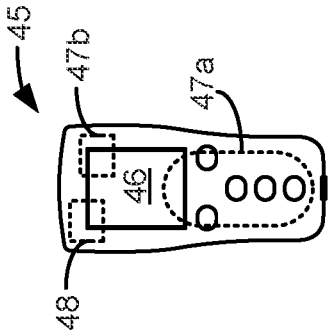

The IPG 100 also includes stimulation circuitry 28 to produce stimulation at the electrodes 16, which may comprise the stimulation circuitry 28 shown earlier (FIG. 3). A bus 118 provides digital control signals from the control circuitry 102 (and possibly from an feature extraction algorithm 140, described below) to one or more PDACs 40$_i$ or NDACs 42$_i$ to produce currents or voltages of prescribed amplitudes (I) for the stimulation pulses, and with the correct timing (PW, F) at selected electrodes. As noted earlier, the DACs can be powered between a compliance voltage VH and ground. As also noted earlier, but not shown in FIG. 4, switch matrices could intervene between the PDACs and the electrode nodes 39, and between the NDACs and the electrode nodes 39, to route their outputs to one or more of the electrodes, including the conductive case electrode 12 (Ec). Control signals for switch matrices, if present, may also be carried by bus 118. Notice that the current paths to the electrodes 16 include the DC-blocking capacitors 38 described earlier, which provide safety by preventing the inadvertent supply of DC current to an electrode and to a patient's tissue. Passive recovery switches $41_i$ (FIG. 3) could also be present, but are not shown in FIG. 5 for simplicity.

IPG 100 also includes sensing circuitry 115, and one or more of the electrodes 16 can be used to sense signals the ESG signal. In this regard, each electrode node 39 is further coupleable to a sense amp circuit 110. Under control by bus 114, a multiplexer 108 can select one or more electrodes to operate as sensing electrodes (S+, S−) by coupling the electrode(s) to the sense amps circuit 110 at a given time, as explained further below. Although only one multiplexer 108 and sense amp circuit 110 are shown in FIG. 5, there could be more than one. For example, there can be four multiplexer 108/sense amp circuit 110 pairs each operable within one of four timing channels supported by the IPG 100 to provide stimulation. The sensed signals output by the sense amp circuitry are preferably converted to digital signals by one or more Analog-to-Digital converters (ADC(s)) 112, which may sample the output of the sense amp circuit 110 at 50 kHz for example. The ADC(s) 112 may also reside within the control circuitry 102, particularly if the control circuitry 102 has A/D inputs. Multiplexer 108 can also provide a fixed reference voltage, Vamp, to the sense amp circuit 110, as is useful in a single-ended sensing mode (i.e., to set S− to Vamp).

So as not to bypass the safety provided by the DC-blocking capacitors 38, the inputs to the sense amp circuitry 110 are preferably taken from the electrode nodes 39. However, the DC-blocking capacitors 38 will pass AC signal components (while blocking DC components), and thus AC components within the ESG signals being sensed (such as the ECAP and stimulation artifact) will still readily be sensed by the sense amp circuitry 110. In other examples, signals may be sensed directly at the electrodes 16 without passage through intervening capacitors 38.

As noted above, it is preferred to sense an ESG signal differentially, and in this regard, the sense amp circuitry 110 comprises a differential amplifier receiving the sensed signal S+(e.g., E8) at its non-inverting input and the sensing reference S− (e.g., E9) at its inverting input. As one skilled in the art understands, the differential amplifier will subtract S− from S+ at its output, and so will cancel out any common mode voltage from both inputs. This can be useful for example when sensing ECAPs, as it may be useful to subtract the relatively large scale stimulation artifact 134 from the measurement (as much as possible) in this instance. That being said, note that differential sensing will not completely remove the stimulation artifact, because the voltages at the sensing electrodes S+ and S− will not be exactly the same. For one, each will be located at slightly different distances from the stimulation and hence will be at different locations in the electric field 130. Thus, the stimulation artifact 134 can still be sensed even when differential sensing is used. Examples of sense amp circuitry 110, and manner in which such circuitry can be used, can be found in U.S. Patent Application Publications 2019/0299006, 2020/0305744, 2020/0305745; and International Patent Publication No. WO 2021/026151.

The digitized ESG signal from the ADC(s) 112—inclusive of any detected ECAPs and stimulation artifacts—is received at a feature extraction algorithm 140 programmed into the IPG's control circuitry 102. The feature extraction algorithm 140 analyzes the digitized sensed signals to determine one or more ECAP features, and one or more stimulation artifact features, as described for example in International Patent Application Publication No. WO 2020/251899.

Such features may generally indicate the size and shape of the relevant signals, but may also be indicative of other factors (like ECAP conduction speed). One skilled in the art will understand that the feature extraction algorithm 140 can comprise instructions that can be stored on non-transitory machine-readable media, such as magnetic, optical, or solid-state memories within the IPG 100 (e.g., stored in association with control circuitry 102).

For example, the feature extraction algorithm 140 can determine one or more neural response features (e.g., ECAP features), which may include but are not limited to:

a height of any peak (e.g., N1);

a peak-to-peak height between any two peaks (such as from N1 to P2);

a ratio of peak heights (e.g., N1/P2);

a peak width of any peak (e.g., the full-width half-maximum of N1);

an area or energy under any peak;

a total area or energy comprising the area or energy under positive peaks with the area or energy under negative peaks subtracted or added;

a length of any portion of the curve of the ECAP (e.g., the length of the curve from P1 to N2);

any time defining the duration of at least a portion of the ECAP (e.g., the time from P1 to N2);

a time delay from stimulation to issuance of the ECAP, which is indicative of the neural conduction speed of the ECAP, which can be different in different types of neural tissues;

a conduction speed (i.e., conduction velocity) of the ECAP, which can be determined by sensing the ECAP as it moves past different sensing electrodes;

a rate of variation of any of the previous features, i.e., how such features change over time;

a power (or energy) determined in a specified frequency band (e.g., delta, alpha, beta, gamma, etc.) determined in a specified time window (for example, a time window that overlaps the neural response, the stimulation artifact, etc.);

any mathematical combination or function of these variables;

Such ECAP features may be approximated by the feature extraction algorithm 140. For example, the area under the curve may comprise a sum of the absolute value of the sensed digital samples over a specified time interval. Similarly, curve length may comprise the sum of the absolute value of the difference of consecutive sensed digital samples over a specified time interval. ECAP features may also be determined within particular time intervals, which intervals may be referenced to the start of simulation, or referenced from within the ECAP signal itself (e.g., referenced to peak N1 for example).

In this disclosure, ECAP features, as described above, are also referred to as spinal neural features or neural response features. This is because such ECAP features contain information relating to how various neural elements in the spine are excited/recruited during stimulation, and in addition, how these neural elements spontaneously fired producing spontaneous neural responses as well.

The feature extraction algorithm 140 can also determine one or more stimulation artifact features, which may be similar to the ECAP features just described, but which may also be different to account for the stimulation artifact 134's different shape. Determined stimulation artifact features may include but are not limited to:

a height of any peak;

a peak-to-peak height between any two peaks;

a ratio of peak heights;

an area or energy under any peak;

a total area or energy comprising the area or energy under positive peaks with the area or energy under negative peaks subtracted or added;

a length of any portion of the curve of the stimulation artifact;

any time defining the duration of at least a portion of the stimulation artifact;

a rate of variation of any of the previous features, i.e., how such features change over time;

a power (or energy) determined in a specified frequency band (e.g., delta, alpha, beta, gamma, etc.) determined in a specified time window (for example, a time window that overlaps the neural response, the stimulation artifact, etc.);

any mathematical combination or function of these variables.

Again, such stimulation artifact features may be approximated by the feature extraction algorithm 140, and may be determined with respect to particular time intervals, which intervals may be referenced to the start or end of simulation, or referenced from within the stimulation artifact signal itself (e.g., referenced to a particular peak).

Once the feature extraction algorithm 140 determines one or more of these features, it may then be used to any useful effect in the IPG 100, and specifically may be used to adjust the stimulation that the IPG 100 provides, for example by providing new data to the stimulation circuitry 28 via bus 118. This is explained further in some of the U.S. patent documents cited above. For example, if the distance between the stimulation electrode(s) and the patient's spinal cord changes (for example, because of postural changes, coughing, movement, etc.), the stimulation may be adjusted based on the extracted features to maintain optimum therapeutic stimulation.

This disclosure relates to methods and systems that use neural features for feedback control, such as closed-loop feedback control for programming, adjusting, and maintaining stimulation therapy (e.g., SCS therapy). The disclosed methods and systems are particularly useful during the provision of sub-perception therapy. Sub-perception (also known as sub-threshold or paresthesia-free) therapy involves providing stimulation that the patient does not readily perceive. With traditional paresthesia (or supra-threshold) therapy, patients typically perceive sensations, such as tingling sensations, that accompany stimulation. Such sensations are referred to as paresthesia. Sub-perception therapy involves providing stimulation with lower stimulation amplitudes that do not evoke paresthesia and correspond to amplitudes below perception threshold or at sub-threshold stimulation amplitudes. While the disclosed methods and systems are particularly useful for sub-perception therapy, they may also be used to maintain supra-threshold therapy as well.

Aspects of programming stimulation parameters, such as choosing which electrodes to use to deliver stimulation, stimulation pulse widths, frequencies, amplitudes, and the like, for delivering sub-perception spinal cord stimulation are discussed in U.S. Pat. No. 10,576,828 ("the '828 Patent") and International Patent Application Publication No. WO 2021/178105 ("the '105 Publication"). The contents of the '828 Patent and the '105 Publication are expressly incorporated herein by reference. As described in those incorporated documents, programming stimulation parameters for providing sub-perception therapy to treat a patient's pain can be challenging because the patient does not feel the stimulation, and therefore it can be difficult for the patient to feel whether the stimulation is "covering" their pain and therefore whether the selected electrodes are effective. Further, sub-perception stimulation therapy may require a "wash in" period before it can become effective. A wash in period can take up to a day or more, and therefore sub-perception stimulation may not be immediately effective, making electrode selection more difficult. The incorporated '828 Patent and '105 Publication discuss techniques and algorithms for selecting which electrodes should be active for delivering stimulation for sub-perception pain relieving modalities. The process of searching for the best electrodes for providing stimulation is sometimes referred to as "sweet spot" searching. The incorporated '828 Patent and '105 Publication also discuss regimes of parameters such as pulse widths and frequencies that provide fast acting sub-perception therapy, that is, sub-perception therapy that has a relatively fast wash-in period. Embodiments of the sub-perception stimulation modalities described in the incorporated documents use low frequencies, for example, frequencies of 130 Hz or less. Various modeling paradigms for facilitating sweet spot searching and parameter discovery are described in the incorporated documents.

Figure 6:
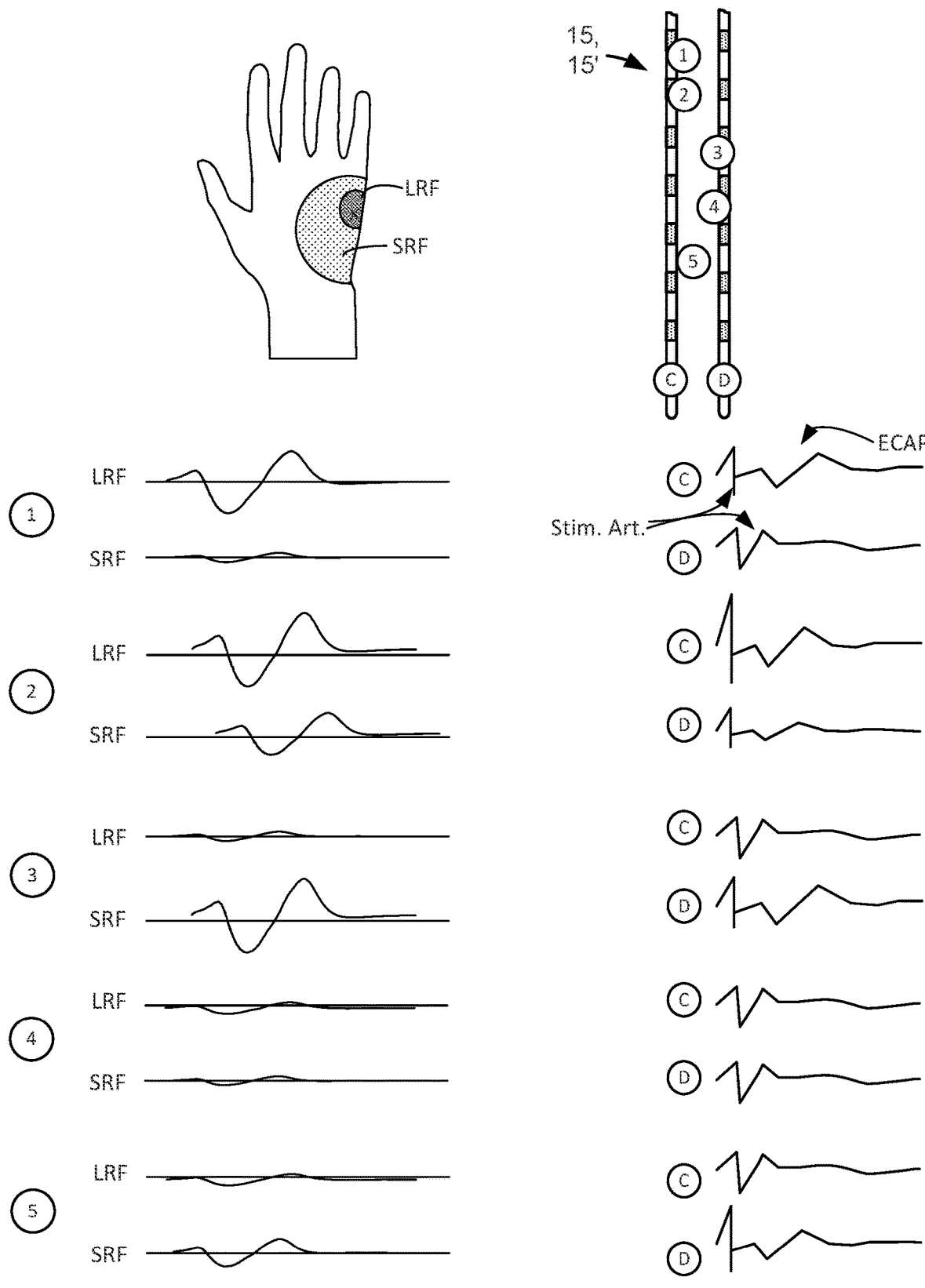
FIG. 6 shows retrograde evoked potentials recorded from a local receptive field (LRF) and from a surrounding receptive field (SRF) with respect to a patient's pain center, as well as ECAPs recorded using spinal electrode contacts.

The inventors have discovered that fast acting sub-perception therapy may be facilitated by exploiting a mechanism of action (MOA) that involves using SCS to activate neural elements involved in surround inhibition. FIG. 6 shows an illustration of a patient's hand. Note that the patient's hand is illustrated as an example of a peripheral location at which the patient might experience pain, but the disclosure relates to any peripheral location on the patient's body. Assume that the patient experiences pain at a location (i.e., a locus) marked by the "x" in a region of their hand, referred to herein as a local receptive field (LRF). The illustration of FIG. 6 also shows an area surrounding the LRF, referred to herein as a surrounding receptive field (SRF). Afferent nerve fibers from each of the LRF and the SRF travel through peripheral nerves to the spinal cord. The fibers from the LRF and SRF may participate differently from one another in various networks in the dorsal horn. See, e.g., Zhang, et al., "Modeling effects of spinal cord stimulation on wide-dynamic range dorsal horn neurons: influence of stimulation frequency and GABAergic inhibition," J. Neurophysiol. 115: 552-67, 2014. Delivering electrical stimulation to dorsal column collaterals of Aβ-fiber afferents originating only from the LRF does not provide optimum pain relief. However, delivering stimulation to dorsal column collaterals of Aβ-fiber afferents originating from the SRF provides pain relief (with respect to pain centered in the LRF) and can provide fast onset of sub-perception therapy. Accordingly, aspects of the disclosure relate to methods and systems for providing electrical stimulation that activates neural elements of the spinal cord corresponding to the SRF, for example, dorsal column collaterals of Aβ-fiber afferents originating from the SRF. According to some embodiments, pain relief may wash in within a period of one hour or less after beginning the therapeutic stimulation. According to some embodiments, pain relief may wash in within a period of ten minutes or less after beginning the therapeutic stimulation.

FIG. 6 illustrates a pair of electrode leads 15/15'. Assume that the leads 15/15' have been epidurally implanted in the patient. The numbered circles represent five stimulation locations, also referred to herein as center points of stimulation (CPSs). As mentioned above, the stimulation locations may or may not correspond to locations of physical electrode contacts since the anodic and cathodic current may be fractionalized among the various electrode contacts to provide stimulation locations at virtual electrodes. As used herein the terms "electrode configuration" and "configuration of electrode contacts" are used to refer to how anodic and cathodic current is fractionalized among the electrode contacts to provide stimulation at a particular CPS. In other words, the electrode configuration configuration/electrode contact configuration characterizes which electrodes/contacts are active, what is the polarity of each active electrode, and what is the relative strength of each active electrode. There is a configuration of the electrode contacts, i.e., a particular fractionalization of anodic and cathodic currents among the electrode contacts, that provides stimulation at CPS 1. Likewise, there is a configuration of electrode contacts that provides stimulation at CPS 2, and so on.

According to some embodiments, retrograde potentials evoked by spinal stimulation can be recorded at the LRF and SRF at the patient's periphery and used to determine if the spinal stimulation is activating the LRF and/or the SRF. For example, peripheral electrodes may be provided at the LRF and the SRF. Examples of peripheral electrodes may include skin potential electrodes, electromyogram (EMG) electrodes, nerve cuff electrodes, electroneurogram (ENG) electrodes, and the like. Typically, one or more electrodes may be configured to record signals at the LRF. The LRF may be location that the patient has identified as the center of their pain. Also, one or more electrodes may be configured to record signals at the SRF. The SRF is the area of the patient periphery surrounding the patients pain center. The width of the receptive fields may vary from patient to patient and also vary depending on the tactile sensitivity of the location on the patient's body, for example, from between a few millimeters (for example, in the hand) to a few inches (for example, in the forearm and the trunk). According to some embodiments, the widths of the receptive fields may be inferred based on two-point discrimination tests.

FIG. 6 illustrates retrograde potentials recorded at the LRF and SRF for each of the CPSs 1-5. Notice that stimulation using the configuration of electrode contacts that provides stimulation at CPS 1 evokes potentials at the LRF but not at the SRF. Stimulation at CPS 2 evokes potentials at both the LRF and the SRF. Stimulation at CPS 3 primarily evokes potentials at the SRF. Stimulation at CPSs 3 and 4 evoke little potentials at either the LRF or the SRF. As mentioned above, the inventors have determined that stimulation that activates the SRF and/or that activates surround inhibition is likely to provide fast acting sub-perception therapy. Accordingly, embodiments of the disclosed methods and system relate to using recorded retrograde potentials, such as those illustrated in FIG. 6, to determine the best spinal electrode contact configuration for providing sub-perception stimulation. For example, according to some embodiments, the clinician may apply stimulation using a plurality of trial spinal electrode contact configurations. For each configuration the clinician may record retrograde evoked potentials at the LRF and SRF and use those recorded potentials to select the best spinal electrode contact configuration, that is, the spinal electrode contact configuration that best activates surround inhibition, for example. According to some embodiments, the best spinal electrode contact configuration may be the contact configuration that evokes the strongest retrograde evoked potential at the SRF. According to some embodiments, the best configuration may be the one that evokes a certain, predetermined ratio of evoked potential amplitudes at the LRF and SRF. According to some embodiments, a threshold values for the SRF and/or the SRF may be used. According to some embodiments, latencies of the LRF and SRF responses may be used as an indication of LRF or SRF activation. According to some embodiments, patient-elicited measurements, such as quality of sensation, overlap with the painful region, overlap with the painful vs. the surround region, may be used as a proxy and/or as an additional correlate to the LRF and SRF measurements, as well as to the evoked spinal potential measurements discussed below. It should be noted that stimulation that activates surround inhibition may also activate other pathways and/or MOAs as well.

As mentioned above, one or more of the electrode contacts of the electrode leads 15/15' may be configured for recording electrical potentials at the spinal cord, such as neural response signals like ECAPs. In the embodiment illustrated in FIG. 6, assume that spinal potentials are recorded at the electrodes marked as C and D. FIG. 6 illustrates potentials recorded at the spinal electrode contacts C and D for each of the CPSs 1-5. Notice that stimulation having CPS 1 evokes an ECAP that is measured at contact C, but little ECAP and only a stimulation artifact is recorded at contact D. CPS 2 evokes some ECAP at contact C and less ECAP at contact D. CPS 3 evokes a strong ECAP at contact D and little ECAP at contact C. According to some embodiments, features of the recorded neural responses may be extracted, as described above. According to some embodiments, the extracted neural response features can be correlated with the electrode contact configurations (i.e., the stimulation locations) as well as with the retrograde potentials recorded at the LRF and SRF for the stimulation electrode contact configurations. By forming these correlations, the clinician can identify ECAP "signatures" that likely correlate to stimulation of the LRF and/or the SRF. Those correlations can be used to optimize stimulation and/or for recalibration, as described below. Referring again to the ECAPs illustrated in FIG. 6, notice that the ECAPs correlated to CPSs 1 and 3 possess the highest Vpeak-to-peak curve length. That might indicate to the clinician to use electrode configurations corresponding to CPSs 1 and 3 for bipolar, staggered, or other stimulation.

Figure 7:
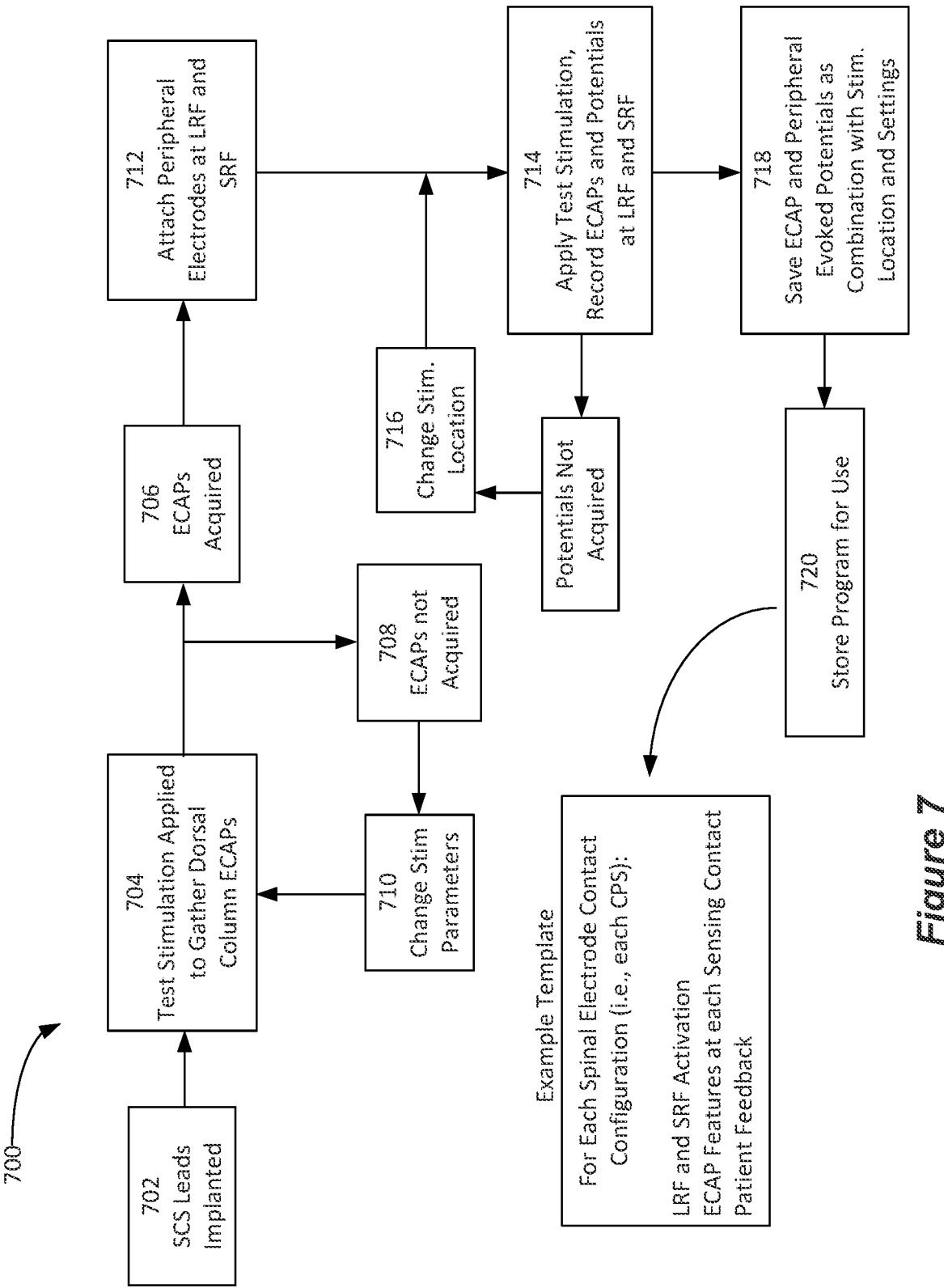
FIG. 7 shows a workflow for an intraoperative calibration procedure for correlating electrode contact configurations, retrograde evoked potentials, and spinal evoked potentials.

FIG. 7 illustrates a workflow 700 for intraoperative or calibration procedure according to a disclosed embodiment. The workflow 700 may be performed in an operating room setting or in a post-operative calibration (i.e., fitting) session, for example. At step 702, one or more SCS leads are implanted epidurally in the patient. The leads may be similar to the leads 15/15' (FIG. 6, e.g.). At step 704, test stimulation is applied at one or more electrode contacts on the lead(s). The purpose of the test stimulation at step 704 is to try to evoke neural responses, such as ECAPs, that can be sensed and recorded at one or more of the electrode contacts of the implanted spinal electrode lead(s). Note that other neural signals instead of, or in addition to, ECAPs may be recorded using the spinal electrode contacts according to the workflow 700; ECAPs are just one example. If ECAPs are not acquired (step 708), then the parameters of the stimulation may be adjusted (step 710). For example, the amplitude of the stimulation may be increased. Once ECAPs are acquired (step 706) peripheral electrodes may be attached to the LRF and SRF, as described above (step 712). At step 714, test stimulation is applied using one or more of the spinal electrode contacts of the electrode lead(s). While applying the test stimulation, ECAPs are recorded using one or more of the spinal electrode contacts. Likewise, retrograde evoked potentials are recorded using the peripheral electrodes at the LRF and SRF. If potentials are not acquired at the peripheral electrodes, then the stimulation positions (i.e., the configuration of the electrode contacts of the spinal electrode lead)

may be changed (step 716). Here the goal is to determine correlations between the stimulation parameters (particularly spinal electrode contact configurations) and the potentials evoked at the LRF and SRF, as measured using the peripheral electrodes. According to some embodiments, electrode contact configurations that evoke primarily LRF retrograde potentials, primarily SRF retrograde potentials, or both LRF and SRF retrograde potentials can be identified. This can provide an indication of whether the spinal electrode contact configuration is providing stimulation to dorsal column collaterals of Aβ-fiber afferents originating from the SRF and is likely to be beneficial for providing fast acting sub-perception therapy. Depending on the patient's indications, the clinician might opt to use stimulation configurations that primarily evoke retrograde potentials in the SRF. Other indications might suggest using stimulation configurations that evoke both SRF and LRF potentials. Other indications might suggest focusing on stimulation that evokes LRF potentials.

At step 718, the ECAPs and/or whatever extracted ECAP features are obtained are saved along with the corresponding retrograde evoked potentials recorded using the peripheral electrodes at the LRF and SRF. At step 720, the programs used during steps 714 and 718 are saved for use, for example, in programming fast acting sub-perception therapy. FIG. 7 illustrates an example template that may be saved for each spinal electrode contact configuration (i.e., stimulation location). An extent of LRF and SRF activation may be saved for each electrode contact configuration. The extent of LRF and SRF activation may be determined from the recorded retrograde evoked potentials. The actual signals may be stored and/or features of the signals (such as peak heights, curve lengths, amplitudes, etc.) for each of the LRF and SRF recordings may be saved. By knowing the relative LRF and SRF activation measurements for each spinal electrode configuration (i.e., stimulation location), the clinician can predict which electrode configurations are likely to activate surround inhibition and be useful for delivering sub-perception therapy. For example, the clinician may use the spinal electrode configurations primarily associated with SRF activation to program sub-perception therapy. The example template for each stimulation configuration also includes the ECAP features determined from ECAPs (or other neural responses) sensed at the one or more sensing electrodes. Correlating the ECAP features with the LRF and SRF activation and the stimulating electrode contact configuration provides an indication of how activation of spinal cord neural elements that project to the LRF and/or SRF are reflected in potentials sensed at the dorsal columns. Thus, the ECAP features are correlated with the extent of activation of surround inhibition. Since the ECAPs are measured at the same lead used for stimulation, changes in the ECAP can be used to infer changes to, or loss of, stimulation coverage, as explained further below. The template may also comprise information, such as patient feedback/therapy ranking for each of the electrode contact configurations. The clinician can use the templates for each of the spinal electrode contact configurations to determine which configurations to use for chronic therapy. The parameters (such as amplitude, pulse width, frequency, etc.) for the therapeutic stimulation may be different than the parameters used during the calibration workflow 700. According to some embodiments, the sub-perception stimulation parameters may be informed using the techniques described in the incorporated '828 Patent and the '105 Publication.

Figure 8:
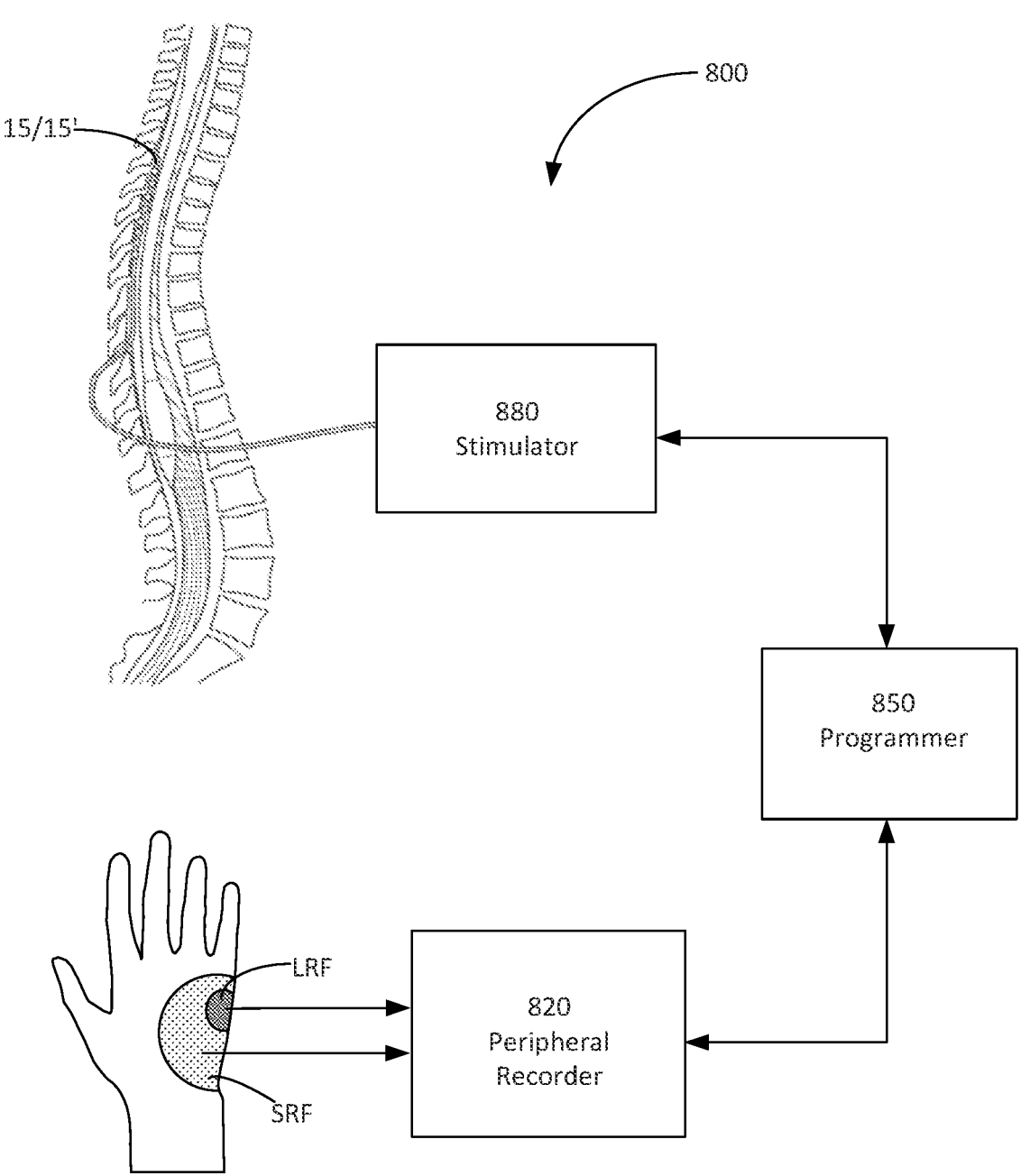
FIG. 8 shows a system for carrying out the workflow illustrated in FIG. 7.

FIG. 8 illustrates a schematic of a system 800 for performing the workflow 700 (FIG. 7). The system 800 may be used in an operating room setting, for example, during the implantation of the electrode leads 15/15'. The system 800 may also be used in a postoperative clinical setting, for example, during a fitting or programming process, as described above. The system comprises a programmer 850, which may be an improved or expanded embodiment of a clinician programmer 50 (e.g., FIG. 4). The programmer 850 may be configured for controlling a stimulator 880, which may be an ETS 80 (FIG. 4) or similar device. The stimulator provides stimulation to the patient's spinal cord using electrode contacts configured upon electrode leads 15/15' that are implantable in the patient's epidural space. The stimulator 880 may also be configured with circuitry (such as sensing circuitry 115, FIG. 5) for recording electrical potentials, such as ECAPs and other neural/electrical activity using one or more electrode contacts of the lead(s) 15/15'. The stimulator 880 may be configured with one or more algorithms, such as the feature extraction algorithm 140 (FIG. 5) for extracting features of the signals recorded using the spinal electrode contacts, as described above. Alternatively (or additionally), such feature extraction may be performed using algorithms and features configured within the programmer 850. The system 800 may also comprise a peripheral recorder 820, which is configured to record potentials sensed using peripheral electrodes, such as peripheral electrodes configured at the patient's LRF and/or SRF. The peripheral recorder 820 comprises the appropriate interface(s), analogue-to-digital converters (ADCs), etc., for recording the peripheral electrode signals and providing them to the system 800. It should be noted that, while the programmer 850, stimulator 880, and peripheral recorder 820 are illustrated as being embodied in separate boxes, one or more of those components may be combined as a single piece of equipment. One or more components of the system 800 may be configured, for example by executing programming code stored in non-transitory computer-readable media, for performing one or more aspects of the methods described herein. For example, the system 800 may be configured with one or more GUIs configured to step a clinician through the steps of the workflow 700 and/or other workflows and methods described herein. For example, the system may be configured to adjust stimulation parameters (such as test stimulation parameters), acquire and extract features of ECAPs (or other electrical signals recorded using the spinal electrode contacts), acquire retrograde evoked potentials recorded using the peripheral electrodes, adjust spinal electrode contact configurations (i.e., stimulation location, including MICC steering of the center-point of stimulation), and make and save correlations between all of these aspects.

Figure 9:
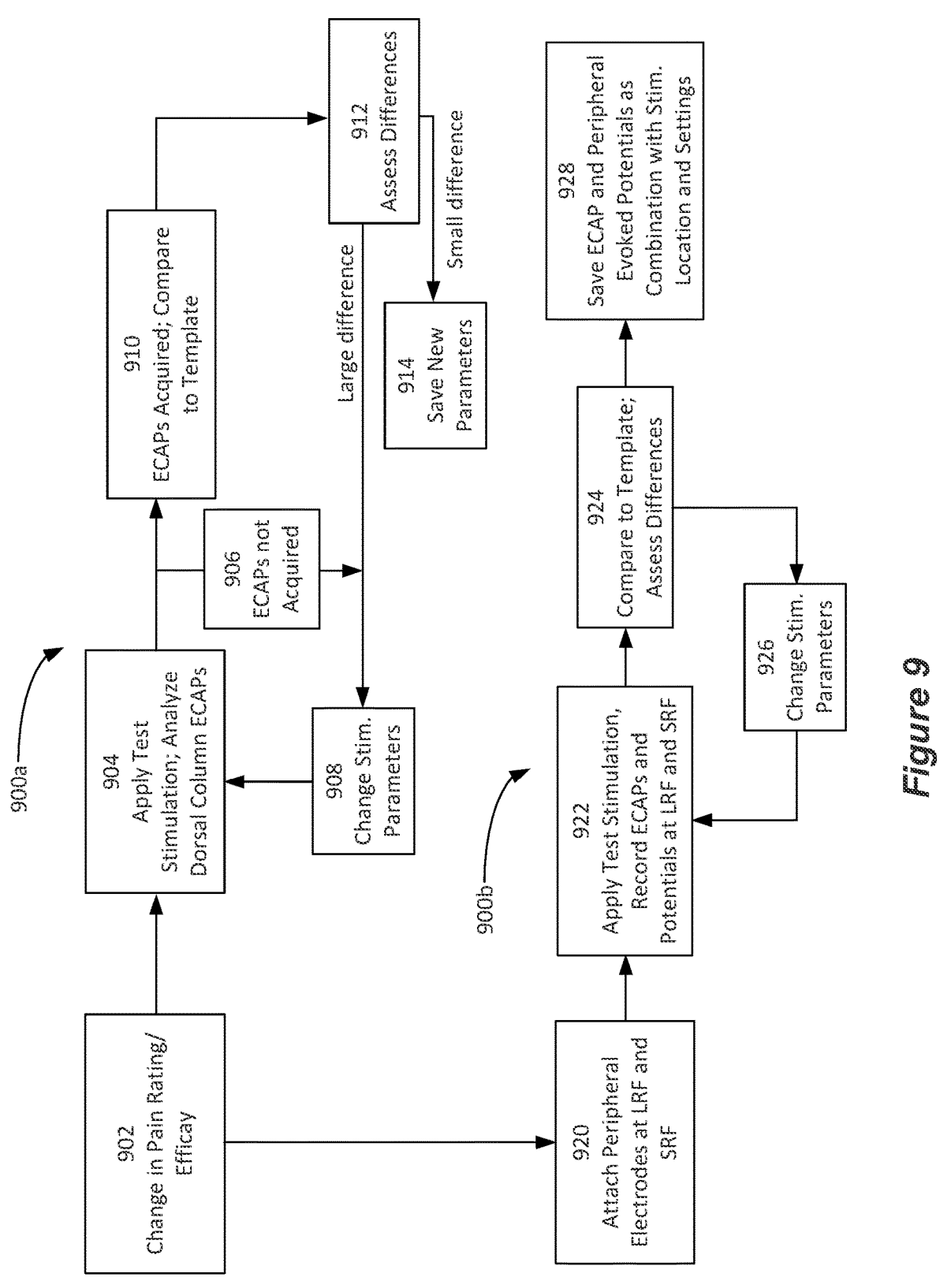
FIG. 9 shows a workflow for adjusting stimulation parameters for maintaining surround inhibition.

FIG. 9 illustrates two workflows 900a and 900b for outpatient methods for adjusting/recalibrating stimulation, for example, when the efficacy a patient's stimulation program decreases. Workflow 900a uses ECAP features (or other spinally-recorded neural response features), for example as determined using the calibration workflow 700 (FIG. 7). The patient's IPG may be configured to perform aspects of the workflow 900a, for example using algorithms stored in the IPG. The workflow 900b requires the patient to use peripheral electrodes to remeasure retrograde evoked potentials at the LRF and SRF, similarly to the workflow 700. The workflow 900b may be performed using the patient's external controller 45 (FIG. 4) which may be configured to record and process potentials recorded using the peripheral electrodes. Alternatively, the patient may be instructed to return to their clinician, who may use a system, such as system 800 (FIG. 8) to perform the workflow 900b.

Referring to the workflow 900a, at step 902 a change in the efficacy of the patient's therapy is detected. According to some embodiments, the patient's therapy may comprise sub-perception therapy. The patient may periodically evaluate their therapy, for example, by using their external controller or another device to record an efficacy rating, pain rating, or the like. According to some embodiments, the algorithm may use such ratings to detect a decline in efficacy and to institute the workflow 900a. At step 904, when a decline in efficacy is detected, the IPG may measure ECAPs (or other neural responses) using one or more spinal electrode contacts. This may involve issuing test stimulation that may be different than the stimulation provided by the patient during chronic therapy. If ECAPs are not detected, then the algorithm may change the stimulation parameters (i.e., electrode configuration, amplitude, pulse width, frequency, and the like) in an attempt to acquire ECAPs (steps 906 and 908). One or more methods known in the art to check for lead migration might also be used at this point. At step 910, once ECAP recordings are acquired, the recorded ECAPs (and/or ECAP features) are compared to the ECAPs/features of the template saved from workflow 700 (FIG. 7). Recall that the templates saved from workflow 700 provide correlations be between ECAPs/features recorded using one or more spinal electrode contacts and stimulation electrode contact configurations that activate desired amounts of the LRF and/or SRF. Thus, assessing the differences (step 912) between the recorded ECAPs/features and the template ECAPs/features can provide an indication of whether the present stimulation is activating the LRF and/or SRF. If the differences between the recorded ECAPs/features and the template ECAPs/features are large, then the algorithm 900a can use one or more closed-loop feedback control algorithms (e.g., Kalman filtering algorithms, heuristic algorithms, simple threshold model, proportional-integral-derivative (PID) controller models, and the like) to change the stimulation parameters (step 908) to try to recover the template ECAP/features correlated with the desired LRF and/or SRF activation. When the stimulation parameters (particularly the stimulation electrode contact configuration) have been adjusted to best recover the template ECAP/features, then the new parameters can be saved (step 914). Accordingly, the workflow 900a uses ECAP (or other neural response) features as a feedback variable to adjust the stimulating contact configuration to attempt to recover stimulation that provides stimulation to neural elements, such as dorsal column collaterals of Aβ-fiber afferents originating from the SRF and is likely to be beneficial for providing fast acting sub-perception therapy. Again, according to some embodiments, the goal is to recover stimulation contact configurations that activate surround inhibition. Those stimulation contact configurations can be used to provide sub-perception therapy that has a fast wash-in time.

Referring to workflow 900b, at step 902 a change in the efficacy of the patient's therapy is detected. The change may be detected based on patient ranking information, as described above. Alternatively, according to some embodiments, the IPG may be programmed to periodically apply test stimulation and compare recorded ECAP features to template ECAPs to determine if the stimulation configuration has changed. At step 920 the patient is instructed to attach peripheral electrodes at the LRF and SRF. At step 922, test stimulation is applied, ECAPs (and/or ECAP features), and retrograde evoked potentials at the peripheral LRF and SRF locations are recorded. At step 924 the recorded ECAPs, and LRF/SRF potentials are compared to the template values to assess differences. At step 926 the stimulation parameters, for example the stimulating electrode contact configurations, may be adjusted based on the comparison. According to some embodiments, the goal is to recover stimulation that provides stimulation to neural elements, such as dorsal column collaterals of Aβ-fiber afferents originating from the SRF and is likely to be beneficial for providing fast acting sub-perception therapy. Again, according to some embodiments, the goal is to recover stimulation contact configurations that activate surround inhibition. At step 928, once appropriate stimulation parameters are recovered, the stimulation settings (including electrode contact configurations), ECAPs/ECAP features, and peripheral evoked potentials are saved. As mentioned above, these measurements may be correlated with patient-elicited measurements such as quality of sensation, overlap with painful the region, overlap with painful vs. surround region, etc.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of providing sub-perception electrical stimulation to a patient's spinal cord to treat pain in the patient using one or more electrode leads implantable in a spinal column of the patient, each electrode lead comprising a plurality of spinal electrode contacts, the method comprising:
    determining a first configuration of the spinal electrode contacts for providing sub-perception stimulation to the patient, wherein the first configuration is configured to provide stimulation that activates surround inhibition with respect to the pain, and
    using the first configuration of electrodes to provide stimulation to the patient, wherein the stimulation is below a perception threshold of the patient, activates surround inhibition, and provides pain relief to the patient,
    wherein determining the first configuration of the electrode contacts comprises:
        determining a locus of the pain,
        using two-point discrimination to determine a surround receptive field (SRF) with respect to the locus,
        using a plurality of different trial configurations of the spinal electrode contacts to provide stimulation to the patient,
        for each trial configuration, using a first one or more peripheral electrodes to record neural responses evoked at the SRF for the stimulation using that trial configuration, and
        using the recorded SRF neural responses to determine the first configuration.

2. The method of claim 1, wherein the pain relief washes in in a period of one hour or less after beginning to provide the stimulation.

3. The method of claim 1, wherein the pain relief washes in in a period of ten minutes or less after beginning to provide the stimulation.

4. The method of claim 1, wherein determining the first configuration further comprises:
    determining a local receptive field (LRF) with respect to the locus, for each trial configuration, using a second one or more peripheral electrodes to record neural responses evoked at the LRF for the stimulation using that trial configuration, and using the recorded LRF neural responses and the recorded SRF neural responses to determine the first configuration.

5. The method of claim 4, wherein using the recorded LRF neural responses and the recorded SRF neural responses to determine the first configuration comprises using the recorded LRF neural responses and the recorded SRF neural responses to predict which of the trial configurations most strongly activates surround inhibition.

6. The method of claim 4, wherein using the recorded LRF neural responses and the recorded SRF neural responses to determine the first configuration comprises:

determining a configuration that evokes the greatest SRF neural response and selecting that configuration as the first configuration.

7. The method of claim 4, wherein using the recorded LRF neural responses and the recorded SRF neural responses to determine the first configuration comprises:

determining a configuration that evokes a ratio of SRF/LRF neural responses that exceeds a predetermined threshold value.

8. The method of claim 4, wherein using the recorded LRF neural responses and the recorded SRF neural responses to determine the first configuration comprises comparing one or more of the recorded LRF neural responses and the recorded SRF neural responses to a predetermined threshold.

9. The method of claim 5, further comprising:

for each trial configuration:

using one or more of the spinal electrode contacts to record spinal neural responses evoked in the spinal cord by the stimulation that trial configuration, and saving a template comprising data indicative of the LRF neural response, the SRF neural response, and the spinal neural responses to stimulation at that trial configuration.

10. The method of claim 9, further comprising:

while providing sub-perception stimulation to the patient receiving an indication of a decline in efficacy of the stimulation, and using the template to adjust the stimulation.

11. The method of claim 10, wherein adjusting the stimulation comprises determining a second configuration of the spinal electrode contacts and using the second configuration to provide sub-perception stimulation to the patient.

12. The method of claim 1, further comprising:

using the first configuration to provide test stimulation the patient, and using one or more of the spinal electrode contacts to record spinal neural responses evoked in the spinal cord by the test stimulation.

13. The method of claim 12, further comprising using the spinal neural responses in a closed-loop feedback control algorithm to adjust the sub-perception stimulation.

14. The method of claim 13, wherein adjusting the sub-perception stimulation comprises determining a second configuration of the spinal electrode contacts and using the second configuration to provide sub-perception stimulation to the patient.

15. A system for providing sub-perception electrical stimulation to a patient's spinal cord to treat pain in the patient using one or more electrode leads implantable in a spinal column of the patient, each electrode lead comprising a plurality of spinal electrode contacts, the system comprising:

a neurostimulator that is connectable to the one or more electrode leads, and control circuitry configured to:

determine a first configuration of the spinal electrode contacts for providing sub-perception stimulation to the patient, wherein the first configuration is capable of providing stimulation that activates surround inhibition with respect to the pain, and cause the neurostimulator to use the first configuration of electrodes to provide stimulation to the patient, wherein the stimulation is below a perception threshold of the patient, activates surround inhibition, and provides pain relief to the patient, wherein determining the first configuration of the electrode contacts comprises:

determining a locus of the pain, using two-point discrimination to determine a surround receptive field (SRF) with respect to the locus, using a plurality of different trial configurations of the spinal electrode contacts to provide stimulation to the patient, for each trial configuration, using a first one or more peripheral electrodes to record neural responses evoked at the SRF for the stimulation using that trial configuration, and using the recorded SRF neural responses to determine the first configuration.

16. The system of claim 15, wherein determining the first configuration further comprises:

determining a local receptive field (LRF) with respect to the locus, for each trial configuration, using a second one or more peripheral electrodes to record neural responses evoked at the LRF for the stimulation using that trial configuration, and using the recorded LRF neural responses and the recorded SRF neural responses to determine the first configuration.

17. The system of claim 16, wherein using the recorded LRF neural responses and the recorded SRF neural responses to determine the first configuration comprises using the recorded LRF neural responses and the recorded SRF neural responses to predict which of the trial configurations most strongly activates surround inhibition.

18. The system of claim 16, wherein using the recorded LRF neural responses and the recorded SRF neural responses to determine the first configuration comprises:

determining a configuration that evokes a ratio of SRF/LRF neural responses that exceeds a predetermined threshold value.

* * * * *